US007010353B2

(12) United States Patent
Gan et al.

(10) Patent No.: US 7,010,353 B2
(45) Date of Patent: Mar. 7, 2006

(54) NON-INVASIVE CAPACITIVELY COUPLED ELECTRICAL STIMULATION DEVICE FOR TREATMENT OF SOFT TISSUE WOUNDS

(75) Inventors: Jean C. Gan, Morris Township, NJ (US); Bruce J. Simon, Mountain Lakes, NJ (US); Jay Penchina, Allendale, NJ (US)

(73) Assignee: EBI, L.P., Parsippany, NJ (US)

( * ) Notice: Subject to any disclaimer, the term of this patent is extended or adjusted under 35 U.S.C. 154(b) by 458 days.

(21) Appl. No.: 10/041,850

(22) Filed: Jan. 7, 2002

(65) Prior Publication Data

US 2003/0130707 A1    Jul. 10, 2003

(51) Int. Cl.
*A61N 1/36* (2006.01)

(52) U.S. Cl. .......................................... 607/50; 607/76
(58) Field of Classification Search .................. 607/50, 607/51, 52, 76, 2
See application file for complete search history.

(56) References Cited

U.S. PATENT DOCUMENTS

| | | | |
|---|---|---|---|
| 4,461,300 A | | 7/1984 | Christensen |
| 4,487,834 A | * | 12/1984 | Brighton .................. 435/173.8 |
| 4,535,775 A | * | 8/1985 | Brighton et al. .............. 607/51 |
| 4,738,250 A | * | 4/1988 | Fulkerson et al. ............ 607/50 |
| 4,846,181 A | | 7/1989 | Miller |
| 4,895,154 A | | 1/1990 | Bartelt et al. |
| 4,919,138 A | | 4/1990 | Nordenstroöm |
| 4,982,742 A | | 1/1991 | Claude |
| 4,993,413 A | | 2/1991 | McLeod et al. |
| 5,014,699 A | * | 5/1991 | Pollack et al. ................. 607/2 |
| 5,038,780 A | | 8/1991 | Boetzkes |
| 5,117,826 A | | 6/1992 | Bartelt et al. |
| 5,158,081 A | | 10/1992 | McWhorter et al. |
| 5,324,314 A | | 6/1994 | Boetzkes |
| 5,433,735 A | | 7/1995 | Zanakis et al. |
| 5,458,626 A | | 10/1995 | Krause |
| 5,607,461 A | | 3/1997 | Lathrop |
| 5,738,521 A | * | 4/1998 | Dugot ........................ 433/173 |
| 5,788,682 A | | 8/1998 | Maget |
| 5,814,094 A | | 9/1998 | Becker et al. |
| 5,861,016 A | | 1/1999 | Swing |
| 5,974,342 A | | 10/1999 | Petrofsky |
| 6,016,450 A | | 1/2000 | Crock |
| 6,048,301 A | | 4/2000 | Sabuda |

(Continued)

OTHER PUBLICATIONS

Kloth LC and McCullock JM. Promotion of wound healing with electrical stimulation. Advances in Wound Care 9(5): 42-45, 1996.

(Continued)

*Primary Examiner*—Kennedy Schaetzle
(74) *Attorney, Agent, or Firm*—William F. Bahret

(57) ABSTRACT

A method for treating a soft tissue wound is provided and includes the steps of providing a signal generator in electrical communication with first and second electrodes, disposing the first and second electrodes on a skin surface on opposing sides of the soft tissue wound and applying an electric field in the soft tissue wound by generating a voltage at a frequency within a range of 20 to 100 kHz and having a symmetrical waveform with an amplitude within a range of 0.1 to 20 volts peak to peak through said first and second electrodes. In accordance with a first preferred embodiment the signal generator is an AC generator generating a sine wave voltage and in accordance with second and third preferred embodiments, the signal generator is a bipolar DC generator, all generating a symmetrical waveform at a frequency of 60 kHz, with an amplitude of about 5 volts peak to peak.

21 Claims, 2 Drawing Sheets

U.S. PATENT DOCUMENTS

| | | | |
|---|---|---|---|
| 6,083,250 A | * | 7/2000 | Lathrop ................... 607/50 |
| 6,132,357 A | | 10/2000 | Sabuda |
| 6,132,362 A | | 10/2000 | Tepper et al. |
| 2002/0128641 A1 | * | 9/2002 | Underwood et al. .......... 606/32 |

OTHER PUBLICATIONS

Mohr T. Akers TM, Landry RL. Effect of high voltage stimulation on edema reduction in the rat hind limb. Phys Ther 67:1703-8, 1987.

Brown M, McDonnell MK, Menton DN. Polarity effects on wound healing using electrical stimulation in rabbits. Arch Phys Med Rehabil 70:624-7, 1989.

Brown M. Gogia PP, Sinacore Dr. High voltage galvanic stimulation on wound healing in guinea pigs: Longer-term effects. Arch Phys Med Regabil 76:1134-7, 1995.

Reed BV. Effect of high voltage pulsed electrical stimulation on microvascular permeability to plasma proteins: A possible mechanism in minimizing edema. Phys Ther 68:491-5, 1988.

Kincaid CB, Lavoie KH. Inhibition of bacterial growth in vitro following stimulation with high voltage, monophasic, pulsed current. Phys Ther 69:651-5, 1989.

Laatsh LJ, Ong PC, Kloth LC. In vitro effects of two silver electrodes on select wound pathogens. J. Cin Electrophysiol 7:10-5, 1995.

Bourguignon GJ, Bourguignon LY. Electric stimulation of protein and DNA synthesis in human fibroblasts. FASEB J 1:398-402, 1987.

Cruz NI, Bayron FE, Suarey AJ. Accelerated healing of full-thickness burns by the use of high-voltage pulsed galvanic stimulation in the pig. Ann Plast Surg 23:49-54, 1989.

Brown M, Gogia PP. Effects of high voltage stimulation on cutaneous wound healing in rabbits. Phys Ther 67:662-7, 1987.

* cited by examiner

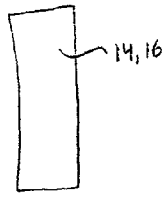
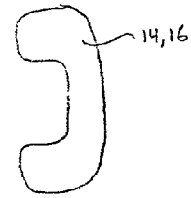
Fig. 4A    Fig. 4B    Fig. 4C
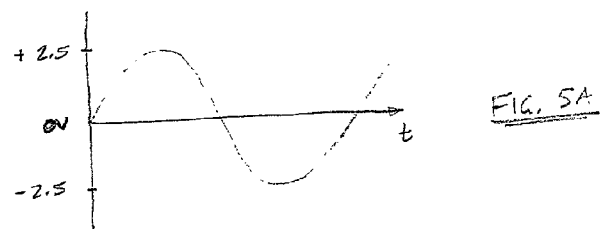
Fig. 5A
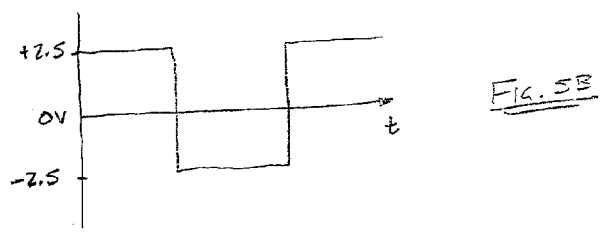
Fig. 5B
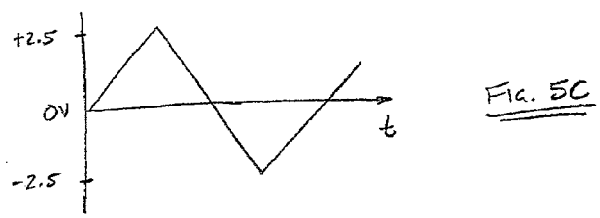
Fig. 5C

NON-INVASIVE CAPACITIVELY COUPLED ELECTRICAL STIMULATION DEVICE FOR TREATMENT OF SOFT TISSUE WOUNDS

FIELD OF THE INVENTION

The present invention relates to wound treatment and more particularly to a method and device for promoting healing of soft tissue wounds.

BACKGROUND OF THE INVENTION

Chronic wounds, such as pressure ulcers, venous ulcers and diabetic ulcers, are significant public health concerns. Within the United States, the annual incidence of such chronic wounds is greater than 7 million. Further, the incidence of these chronic wounds increases as much as 14% per year. This is particularly true for diabetic ulcers, which afflict about 15% of the 16 million diabetics in the United States. Each year, approximately 85,000 lower-extremity amputations are performed as a result of treatment failure of diabetic ulcers. Such chronic wounds occur in approximately 31% of diabetic patients and take up to 20 weeks to heal. The incidences of venous and pressure ulcers within the United States are estimated to be 1.3 million and 3 million, respectively, with an annual growth rate of about 6%.

Wound healing involves a series of interrelated events including coagulation, inflammation, deposition and differentiation of extracellular matrix, fibroplasia, epithelialization, contraction and remodeling. There are slight differences in the healing process depending on the type of wound. For example, the healing of a chronic pressure ulcer mainly involves deposition of extracellular matrix and contraction. However, a partial-thickness burn wound primarily heals through epithelialization. On the other hand, the healing of diabetic ulcers can be further complicated by other diabetic issues such as neuropathy, poor circulation and decreased response to infection.

Presently, chronic wound patients are faced with a lack of effective treatment options and a high cost of care. Currently available treatment methods for the type of wounds described above include various types of dressings, debridement/irrigation, pressure relieving devices, ultrasound, whirlpool/pulsed lavage, ultraviolet, pulsed frequency radiation, low-energy laser, hyperbaric or topically applied oxygen, cytokine growth factors, antibiotics and topical and systemic drugs. Research has also been centered on developing surgical glues, sealants and dressing, artificial skin and growth factors such as transforming growth factors (TGF-$\beta$), fibroblast growth factor (aFGF and bFGF), platelet-derived growth factor (PDGF), epidermal growth factor (EGF), insulin-like growth factors (IGF-I and IGF-II) and interleukins (IL-1 and IL-2). Other research has focused on reducing the pressure on the soft tissue by designing a variety of wheelchair cushions, pads, shoes, mattresses and beds to distribute the pressure more evenly over the body. Unfortunately, even with the best available wound care procedures, chronic wounds tend to heal very slowly, not heal at all, or even worsen.

An alternative approach to wound healing is the implementation of electrical stimulation. The rationale for using electrical stimulation is based on the fact that the human body has endogenous bioelectric systems that promote wound healing. However, when the body's endogenous bioelectric system is inadequate, external electrical stimulation can be used to supplement the natural bioelectric currents or electric fields for enabling or enhancing wound healing.

The exact mechanism by which capacitively coupled electrical stimulation enhances wound healing is not completely understood. However, it has been found that the biochemical pathway mediating cell response to capacitively coupled electrical stimulation involves the opening of voltage-gated calcium channels that allow a flow of calcium ions into the cell. The subsequent increase in intracellular calcium levels triggers the activation of a host of signal tranduction pathways. These processes include activation of calmodulin and release of several second messenger molecules, such as cyclic adenosine monophosphate (c-AMP) and prostaglandin $E_2$. These molecules activate specific protein kinases including c-AMP-dependent protein kinase, calcium-calmodulin dependent protein kinase and protein kinase-C, which results in increased cell proliferation. Further, capacitively coupled electrical stimulation also promotes local growth factor synthesis, such as transforming growth factor-beta 1 (TGF-$\beta_1$) by the calcium-calmodulin pathway, and can affect different types of growth factor receptors. The growth factor receptors have integrated tyrosine kinase activities, which can activate several intracellular proteins involved in cell proliferation.

There are several disadvantages associated with prior art methods of electrical stimulation for wound healing. One disadvantage is that many prior art methods require placement of one or perhaps two electrodes directly on the soft tissue wound. Such placement increases the probability of bacterial contamination, thereby complicating wound healing and further, acid or base build-up on the electrodes can adversely effect healing in the wound area. Other prior art devices and methods are inconvenient or difficult to employ as a result of their bulk or complexity. For example, several prior art devices require the implementation of several electrodes, whereby one electrode is applied directly over the wound area or immersed in a saline solution containing the body part with the wound and at least one other electrode is positioned on the patient as far away from the wound as possible. This makes extended treatment periods uncomfortable for the patient, as well as, prohibiting free travel of the patient.

Thus, it is desirable to provide an improved electrical stimulation method for promoting wound healing of soft tissue wounds, such as venous, diabetic and pressure ulcers. The method should treat the wound area without actual contact with the wound to reduce the probability of bacterial infection. Further, the method should be simple and inexpensive while effectively treating soft tissue wounds.

SUMMARY OF THE INVENTION

Accordingly, the present invention provides a method for treating a soft tissue wound. The method includes the steps of providing a signal generator in electrical communication with first and second electrodes, disposing the first and second electrodes non-invasively on a skin surface on opposing sides of the soft tissue wound and applying an electric field in the soft tissue wound by generating a voltage signal at a frequency within a range of 20 to 100 kHz and having a symmetrical waveform with an amplitude within a range of 0.1 to 20 volts peak to peak through the first and second electrodes.

In accordance with a preferred embodiment of the present invention, the signal is generated as an AC signal, being a symmetrical sine wave at 60 kHz and an amplitude of about 5 volts peak to peak.

In accordance with an alternative embodiment of the present invention, the signal is generated as a bipolar DC signal having a symmetrical step waveform at a frequency of 60 kHz and an amplitude of about 5 volts peak to peak.

In accordance with yet another alternative embodiment of the present invention, the signal is generated as a bipolar DC signal having a triangular waveform at a frequency of 60 kHz and an amplitude of about 5 volts peak to peak.

Further areas of applicability of the present invention will become apparent from the detailed description provided hereinafter. It should be understood that the detailed description and specific examples, while indicating the preferred embodiment of the invention, are intended for purposes of illustration only and are not intended to limited the scope of the invention.

BRIEF DESCRIPTION OF THE DRAWINGS

The present invention will become more fully understood from the detailed description and the accompanying drawings, wherein:

FIG. 4A is a schematic view of a second embodiment of an electrode design;

FIG. 4B is a schematic view of a third embodiment of an electrode design;

FIG. 4C is a schematic view of a fourth embodiment of an electrode design;

FIG. 5A is a graphical representation of a voltage signal generated by as an AC signal having a symmetric sine waveform;

FIG. 5B is a graphical representation of a bipolar DC signal generated as a DC signal having a symmetric step waveform; and FIG. 5C is a graphical representation of a bipolar DC signal generated as a DC signal having a triangular waveform.

DETAILED DESCRIPTION OF THE PREFERRED EMBODIMENTS

The following description of the preferred embodiments is merely exemplary in nature and is in no way intended to limit the invention, its application, or uses.

Figure 1A:
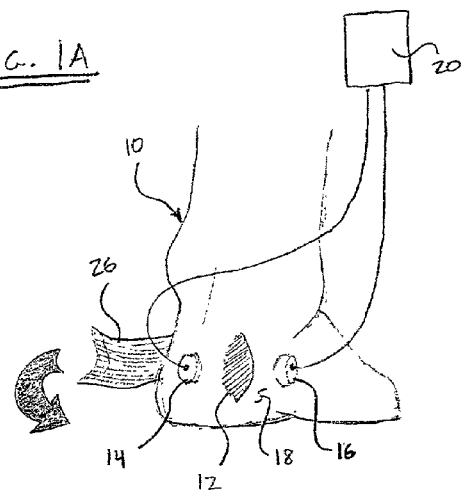
FIG. 1A is a schematic view of a lower body extremity having a soft tissue wound thereon and implementing a treatment method in accordance with the principles of the present invention.
Figure 1B:
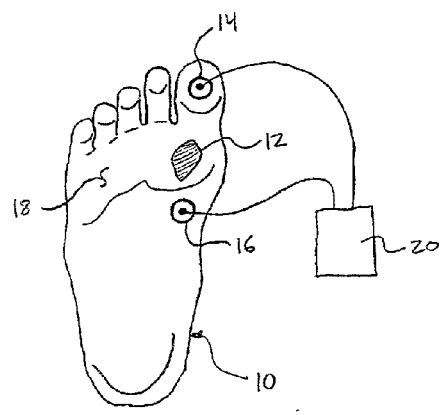
FIG. 1B is a plan view of a base of a foot having a soft tissue wound thereon and implementing a treatment method in accordance with the principles of the present invention.
Figure 2:
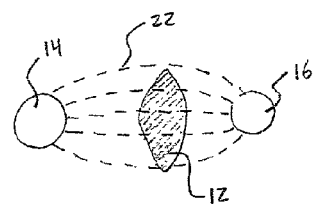
FIG. 2 is a schematic view of an electric field generated by an electrode pair disposed on opposing sides of the soft tissue wound.

With particular reference to FIGS. 1A, 1B and 2, a lower body extremity 10, in this example a foot, includes a soft tissue wound 12, such as, but not limited to a venous ulcer, a pressure ulcer or a diabetic ulcer. First and second electrodes 14,16 are operably attached to a skin surface 18 on opposing sides of the soft tissue wound 12 for creating a capacitive coupling therebetween. While the present discussion is directed toward the first and second electrodes 14,16, it is anticipated that more electrodes may be implemented. The first and second electrodes 14,16 are non-invasively attached to the skin surface 18, whereby neither electrode 14,16 is in direct contact with the soft tissue wound 12. Further, especially in diabetic cases, the first and second electrodes 14,16 are preferably not disposed on pressure points (e.g. heel, ball of foot, etc.). The first and second electrodes 14,16 are in electrical communication with a signal generator 20 that generates a voltage signal therebetween. In this manner, the soft tissue wound 12 is immersed in an electric field 22. In accordance with the present invention, the electric field 22 is generated through application of a voltage at a frequency within a range of 20 to 100 kHz and having symmetrical waveform with an amplitude in the range of 0.1 to 20 volts peak to peak.

In accordance with the requirements of a particular treatment ideology, the electric field 22 may be intermittently generated or continuously generated until full healing of the soft tissue wound 12 occurs. For example, the electric field 22 could be intermittently generated for several hours a day for several days per week until healing of the soft tissue wound 12 occurs. Alternatively, the electric field 22 can be applied for 24 hours per day, 7 days per week until healing of the soft tissue wound 12 occurs, with stoppage for changing batteries in the signal generator 20, bathing, or repositioning the first and second electrodes 14,16 about the soft tissue wound 12.

The signal generator 20 is preferably compact, being easily portable. For example, it is preferred that the signal generator 20 be sufficiently compact, thereby being easily carried by a patient, such as on a belt, in a pocket or by other appropriate means. It is also anticipated that an adherent conducting layer (not shown) is incorporated into a surface of the first and second electrodes 14,16 to maintain good conducting relation and allowing easy adherence and removal of the electrodes 14,16 to/from the skin surface 18. Further, it is anticipated that a tape or bandage 26 can be placed about the first and second electrodes 14,16 to further assist in maintaining correct placement of the first and second electrodes 14,16.

Figure 3A:
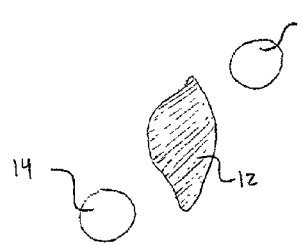
FIG. 3A is a schematic view of a second embodiment of electrode placement about the soft tissue wound.
Figure 3B:
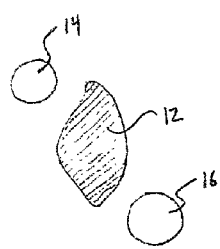
FIG. 3B is a schematic view of a third embodiment of electrode placement about the soft tissue wound.
Figure 3C:
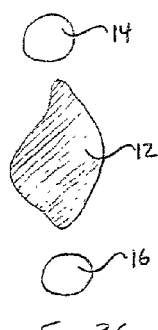
FIG. 3C is a schematic view of a fourth embodiment of electrode placement about the soft tissue wound.

As shown in FIG. 2, in a first embodiment, the first and second electrodes 14,16 are directly disposed on opposite sides of the width of the soft tissue wound 12. With reference to FIGS. 3A through 3C, second, third and fourth embodiments for placement of the first and second electrodes 14,16 are respectively shown. In accordance with the second and third embodiments, the first and second electrodes 14,16 are diagonally disposed on opposite sides of the soft tissue wound 12 (see FIGS. 3A and 3B). In accordance with the fourth embodiment, the first and second electrodes 14,16 are directly disposed on opposite sides of the length of the soft tissue wound 12 (see FIG. 3C). In this manner, the electric field 22 flows through the soft tissue wound 12 at varying angles, thereby enabling all aroung emersion of the soft tissue wound 12 in the electric field 22.

In accordance with a first preferred embodiment, the first and second electrodes generally are circular in shape. With reference to FIGS. 4A through 4C, second, third and fourth embodiments of designs for the first and second electrodes 14,16 are respectively shown. In accordance with the second preferred embodiment, the first and/or second electrode 14,16 may be generally square in shape. In accordance with the third preferred embodiment, the first and/or second electrode 14,16 may be of a generally rectangular shape. In accordance with the fourth preferred embodiment, the first and/or second electrode 14,16 may be provided as having a U-shape. In general, the design of the first and second electrodes 14,16 enables manipulation of the electric field 22. For example, varying the electrode design enables concentration of the electric field 22 in a particular direction or alters the breadth of the electric field 22. Further, it will be appreciated that the first and second electrodes 14,16 are not required to be of the same design and a mix of electrode designs may be implemented.

Generally, the present method provides the steps of providing the signal generator 20 in electrical communication with the first and second electrodes 14,16, disposing the first and second electrodes 14,16 non-invasively on the skin surface 18 on opposing sides of the soft tissue wound 12 and applying the electric field 22 through the soft tissue wound 12 by generating a voltage at a frequency within a range of 20 to 100 kHz and having a symmetrical waveform with an amplitude within a range of 0.1 to 20 volts peak to peak.

With reference to FIGS. 5A through 5C, alternative embodiments of the applied voltage will be described in detail. In accordance with the first preferred embodiment, the signal generator 20 generates an alternating current (AC) to impart a voltage having a sinusoidal waveform. The voltage is symmetrical about a 0V axis and is generated within a frequency range of 20 to 100 kHz. Preferably, however, the voltage is generated at a frequency of 60 kHz. Further, the voltage includes a constant amplitude within a range of 0.1 to 20 volts peak to peak, and preferably about 5 volts peak to peak.

In accordance with the second preferred embodiment, the signal generator 20 generates a bipolar voltage having a symmetrical step waveform. The voltage is symmetrical about a 0V axis and is generated within a frequency range of 20 to 100 kHz. Preferably, however, the voltage is generated at a frequency of 60 kHz. Further, the voltage includes a constant step amplitude within a range of 0.1 to 20 volts peak to peak, and preferably about 5 volts peak to peak.

In accordance with the third preferred embodiment, the signal generator 20 generates a bipolar voltage having a triangular waveform. The voltage is symmetrical about a 0V axis and is generated within a frequency range of 20 to 100 kHz. Preferably, however, the voltage is generated at a frequency of 60 kHz. Further, the voltage includes a constant amplitude within a range of 0.1 to 20 volts peak to peak, and preferably about 5 volts peak to peak.

As detailed herein, the present invention provides several significant advantages. Initially, the present invention enables improved healing of soft tissue wounds through capacitively coupled electric stimulation. This is achieved with reduced treatment time and little discomfort to the patient. Further, non-invasive coupling of the electrodes to the skin surface reduces the risk of added bacterial infection. Finally, the present invention provides a simple, cost-effective soft wound treatment method, thereby significantly reducing the overall costs of patient treatment within the industry. Thus, the apparatus and method of the present invention are advantageous over prior art wound healing apparatuses and methods, such as those requiring invasive contact of electrodes or are bulkier, thereby limiting mobility of a patient during treatment.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of treating a soft tissue wound, comprising:
   identifying a soft tissue wound on a subject;
   indicating the use of capacitively coupled electrical stimulation for treatment of the identified soft tissue wound;
   providing a signal generator in electrical communication with first and second electrodes;
   disposing said first and second electrodes on a skin surface of the subject on opposing sides of the identified soft tissue wound; and
   applying an electric field in the identified soft tissue wound for treatment thereof, said electric field being generated between said first and second electrodes by generating an electrical signal therebetween at a frequency within a range of 20 to 100 kHz and having a symmetrical waveform with an amplitude within a range of 0.1 to 20 volts peak to peak.

2. The method of claim 1, wherein said signal generator is an AC generator generating a sine wave electrical signal.

3. The method of claim 1, wherein said signal generator is a bipolar DC generator generating a symmetrical step waveform.

4. The method of claim 1, wherein said signal generator is a bipolar DC generator generating a triangular waveform.

5. The method of claim 1, further comprising the step of applying said electric field continuously until the soft tissue wound heals.

6. The method of claim 1, further comprising the step of applying said electric field intermittently until the soft tissue wound heals.

7. The method of claim 1, further comprising the step of incorporating an adherent conducting material on said first and second electrodes to maintain good conducting relation and enabling easy adherence and removal of said first and second electrodes to/from said skin surface.

8. The method of claim 1, further comprising the step of applying a bandage about said first and second electrodes for maintaining a position thereof.

9. The method of claim 1, further comprising:
   periodically reconfiguring said first and second electrodes about the soft tissue wound.

10. The method of claim 9, wherein said signal generator is an AC generator generating a sine wave voltage.

11. The method of claim 9, wherein said signal generator is a bipolar DC generator generating a symmetrical step waveform.

12. The method of claim 9, wherein said signal generator is a bipolar DC generator generating a triangular waveform.

13. The method of claim 9, further comprising the step of applying said electric field continuously until the soft tissue wound heals.

14. The method of claim 9, further comprising the step of applying said electric field intermittently until the soft tissue wound heals.

15. The method of claim 9, further comprising the step of incorporating an adherent conducting material on said first and second electrodes to maintain good conducting relation and enabling easy adherence and removal of said first and second electrodes to/from said skin surface.

16. The method of claim 9, further comprising the step of applying a bandage about said first and second electrodes for maintaining a position thereof.

17. A method of healing a soft tissue wound, comprising:
   identifying a soft tissue wound on a subject;

indicating the use of capacitively coupled electrical stimulation for treatment of the identified soft tissue wound;

providing a signal generator in electrical communication with first and second electrodes;

disposing said first and second electrodes on a skin surface proximate to the identified soft tissue wound;

generating a time varying electrical signal with said signal generator;

delivering said electrical signal to said first and second electrodes;

generating an electric field in a region of the identified soft tissue wound, for treatment thereof, upon delivering of said electrical signal to said first and second electrodes, wherein said generating an electric field comprises generating a voltage at a frequency within a range of 20 to 100 kHz and having a symmetrical waveform with an amplitude within a range of 0.1 to 20 volts peak to peak through said first and second electrodes.

18. The method of claim 17, wherein said signal generator is an AC generator generating a sine wave voltage.

19. The method of claim 17, wherein said signal generator is a bipolar DC generator generating a symmetrical step waveform.

20. The method of claim 17, wherein said signal generator is a bipolar DC generator generating a triangular waveform.

21. A method of treating a soft tissue wound, comprising:

providing a signal generator in electrical communication with first and second electrodes;

disposing said first and second electrodes on a skin surface on opposing sides of an identified soft tissue wound; and applying an electric field in the identified soft tissue wound, for treatment thereof, by generating an electrical signal at a frequency within a range of 20 to 100 kHz and having a symmetrical waveform with an amplitude within a range of 0.1 to 20 volts peak to peak through said first and second electrodes.

* * * * *